US00PP17908P3

(12) United States Plant Patent
Sproul

(10) Patent No.: US PP17,908 P3
(45) Date of Patent: Aug. 7, 2007

(54) CLIMBING MINIATURE ROSE PLANT NAMED 'SPROLIFE'

(50) Latin Name: *Rosa hybrida*
Varietal Denomination: SPRolife

(75) Inventor: James Sproul, Bakersfield, CA (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 37 days.

(21) Appl. No.: 11/201,618

(22) Filed: Aug. 11, 2005

(65) Prior Publication Data

US 2007/0039078 P1 Feb. 15, 2007

(51) Int. Cl.
*A01H 5/00* (2006.01)

(52) U.S. Cl. ..... Plt./109

(58) Field of Classification Search ..... Plt./109, Plt./116

See application file for complete search history.

*Primary Examiner*—Kent Bell

(57) ABSTRACT

'SPRolife' is a new and distinct variety of miniature rose plant, classified as a miniature climber. It is primarily identified by its miniature-sized, orange-red and white striped flowers borne in large clusters on long and arching canes with abundant, miniature-sized foliage. The plant can be trained as a climber or allowed to grow freestanding, where its canes will arch and form a large mound or shrub of 5 to 6 feet tall and spreading 3 feet or more from center. The plant has been noted to have very good resistance to powdery mildew.

1 Drawing Sheet

CROSS REFERENCE

This new invention bears resemblance to an earlier cross of 'MACminmo' (U.S. Plant Pat. No. 7,319) by 'FOUmich' (not patented), from this same breeding program. The primary similarity is that both are striped. The unintroduced seedling is pink and ivory while this new invention, 'SPRolife', is orange-red and white.

RIGHTS TO THE INVENTION

Be it known that James A. Sproul of Bakersfield, Calif., claims invention of new and useful improvements in ROSE PLANT/var. 'SPRolife' and following is a clear and exact description of the same.

Genus and species: *Rosa hybrida.*

Varietal denomination: 'SPRolife'.

BACKGROUND OF THE INVENTION

This present invention relates to a new and distinct, tall (or climbing) variety of hardy and well branched type plant of the miniature rose class. This new variety was created by James A. Sproul at his nursery in Bakersfield, Calif., under conditions of careful control and observation, as a result of crossing the following two rose plants:

The seed parent is 'MACminmo' (U.S. Plant Pat. No. 7,319).

The pollen parent is 'JACpoy' (U.S. Plant Pat. No. 9,015).

The objective in making the cross for 'SPRolife', was to get a more exciting coloring on a disease resistant, striped mini climber than the coloring of 'MACminmo'. The seed parent, 'MACminmo', has above average disease resistance and flowers with red white wide and narrow stripes and flecks borne in pyramidal clusters and flowers averaging 14 petals. It is a miniature shrub with arching canes. The pollen parent, 'JACpoy', is a yellow and orange-red blend, clusterflowered, compact rose of the miniature class with good disease resistance to powdery mildew and rust.

The present invention, 'SPRolife', has striped flowers, borne in clusters on long arching canes, similar to its seed parent, 'MACminmo', and with similar flower form. New foliage appears "bronze colored" but not as dark as that of the seed parent, with some light green showing through. The coloring of the flowers of 'SPRolife' is red and white with the red being closer to and the same as the orange-red found in 'JACpoy', rather than the red of its seed parent.

Another trait of this new invention is related to the clusters. In spring, there are more clusters on this new invention, similar to its seed parent, 'MACminmo', with many having 20 and more flowers per cluster. Repeat blooming of the plant is in clusters that may be in pyramidal form as found on 'MACminmo' but more of them having only 5 to 7 flowers, as is more common to 'JACpoy'.

SUMMARY OF THE INVENTION

This present invention relates to a new and distinct variety of the miniature rose class, with well branched, upright and arching plant habit. The characteristics distinguishing it from its parents and from all other varieties of which I am aware are its unique combination of its oranges-red and white striped flowers, the size and form of its clusters of those flowers, the size and petal count of its flowers, its vigorous and arching plant habit and its percentage of seven leaflet leaves. Those varieties that this new invention seems to bear any resemblance to are all offspring of 'MACminmo'. None have all of the above-mentioned unique combination of characteristics.

The variety is further characterized by:

Canes that arch over from the weight of their large clusters of buds and flowers, creating a plant that reaches up to 6 feet wide and with flowering stems branching from those growing to a height of 5 to 6 feet Canes growing 4 to 5 feet and more in length, always terminating in a cluster of flowers before any lateral or flowering stems begin to grow along that cane Clusters having anywhere from 5 to 20 or more buds and flowers An abundance of medium-green leaves generally located around ¾-inch apart the entire length of the canes and flowering stems; these leaves primarily having 7 leaflets New light green growth flushed bronze A plant with tremendous vigor Exceptional resistance to powdery mildew Possible uses: This new invention might be trained as a climber, used as a specimen plant or in borders. It will do well in a very large container but requires frequent watering.

Subsequent to the origination of the cultivar, it was reproduced successfully, asexually, in Bakersfield, Calif., and Arroyo Grande, Calif., by budding as well as by cuttings. The reproductions have run true in all respects.

BRIEF DESCRIPTION OF THE DRAWING

The accompanying color photograph taken in the spring, shows a portion of a plant of this new invention, in full bloom, as grown in Bakersfield, Calif. Buds and blooms in all stages of development are visible as well as new and older foliage and stems.

BOTANICAL DESCRIPTION OF THE PLANT

Genus/species: *Rosa hybrida.*
Commercial class: Miniature rose, climbing.
Varietal denomination: 'SPRolife'.

The following observations, measurements, values and comparisons describe 4 to 5 year old plants of *Rosa hybrida,* 'SPRolife', growing outdoors in Essex County Mass., in 3 gallon, plastic nursery containers, in an artificial soil and compost mixture and fertilized at every other watering, weather permitting, with complete water-soluble plant foods, highest in phosphorus. Color references are made using The Royal Horticultural Society (London, England) Colour Chart, except where common terms of color are used.

FLOWERS

Blooming habit: cyclic, throughout the growing season.

Borne in large clusters. The first flush of bloom in the spring has numerous, huge clusters, often with 20 or more buds and flowers. The remainder of the year, the clusters tend to be smaller with 5 to 9 flowers.

Bud:

*Size.*—⅜ of an inch in length and ⅜ inch diameter at the widest point just before the sepals divide.

*Form.*—Ovoid with a cuspidate apex and an obtuse base.

*Color.*—When sepals first divide the first colors most often seen are white, near 155D, and Fire Red, near 33B.

Sepals:

*Color.*—Outer surface is Lettuce Green, near 144A, flushed with near 183D from the greyed-purple group; inside surface appears a dark yellow-green near 147B.

*Characteristics.*—Shape and size is ovate-lanceolate with a truncate base and an acuminate apex; extending 10/32-to 11/32-inch beyond the tip of the bud just before the sepals start to divide. Inside surface is pubescent; outer surface is matte, coriaceous and glandular. All sepals have ciliate margins.

There are usually 6 sepals, one being somewhat smaller and inside the others. It is not unusual to find one or two dimorphic sepals that have partial characteristics of the petals, including texture, color and form.

Two sepals have one or two very small, linear, foliar appendages near the tip often along only one margin. The size of these two foliated sepals is about 9/32 inch wide and their lengths may be equal, varying from 15/16-inch to 1 2/16-inches and one may be 1/16-inch longer than the other.

Three sepals are slightly smaller, varying between 8/32- and 12/32-inch wide and from 24/32- to 31/32-inch long. The sixth and inner sepal is not more than 7/32-inch wide but may be conjoined with one of the other sepals having a combined width of ⅜-inch about ⅓ of the way up from the base. At that point the conjoined sepals divide into two separate upper portions with the upper portions appearing as the corresponding sepals.

The sepals begin rolling back with the petals. One may then proceed ahead of the petals and when the flower is full open, 3 or 4 sepals continue to roll back until they are parallel with the peduncle, leaving 2 or 3 sepals adjacent to the petals. The sepals detach from the receptacle before the hip begins to form.

Bloom:

*Size.*—At exhibition stage the circumference of the blossom is circular. Its diameter measures 1¾-inches across and its depth is 11/16-inch. When fully expanded it is not circular, measuring 2¼-inches by either 2⅛- or 1 13/16-inches across and 11/16- to ¾-inch deep.

*Form.*—Opens with flat upper profile and cupped lower profile; full open, both the upper and lower profiles are flat and the sides are ruffled.

Petalage under normal conditions in Essex County, Mass., is 23 to 28. In Kern County, Calif., the petal count may be only half that, around 14 petals.

*Petaloids.*—1 to 9 but most often, 4.

Fragrance is slight in the full open bloom.

Petals:

*Texture and appearance.*—Both surfaces are glabrous. The upper surface is velvety and the under surface is satiny.

*Form/shape.*—Outer petals are rotundate to broad fan shaped. Intermediate petals are broad fan shaped and inner petals are narrower and fan shaped. Base is ovate. Margin is entire. The outer edges are rounded with cuspidate apex.

*Length and width of outermost petals.*—Width varies from around ⅞-inch to 1 1/16-inches with 1-inch being the most common width. Length varies from 11/16- to 1 1/16-inches with 15/16-inch being the most common length.

*Arrangement.*—Imbricated.

*Persistence.*—From the time the sepals first divide to open bloom ranges from 4 to 7 days. The petals usually drop off cleanly, 5 to 8 days later.

*Color.*—When sepals divide the reverse is Buttercup Yellow, near 16C, at the base and becoming near 158B from the yellow-white group in the basal area; the outer edges have streaks of a near white from the orange group, near 27D, a whiter white, near 159D, and Coral Pink, near 38D. During the first few days the color of inner and outer petals and the petaloides is the same. The petals have stripes, streaks and flecks of Signal Red, near 43A, and stripes, streaks and flecks of Naples Yellow, near 11C, and Empire Yellow, near 11D. The basal area is Naples Yellow and may be near 11B or 11C or may have both shades of Naples Yellow. The point of attachment is even darker yellow, near 11A. Occasionally the outer petals may be solid Signal Red, down to the basal area, but have never been noticed to be solid yellow or white.

The color on the reverse of the petals is actually showing through from the upper surface, Some areas appear Scarlet, near 43D, and some areas appear Azalea Pink, near 41C, some appear Jasper Red, near 39C and some appear near 11C and some near 11D. The Basal area is near 11B and the point of attachment is near 11A.

When the flower is half blown the outer petals have stripes, streaks and flecks of Capsicum Red, near 33A, the same shade as found in 'JACpoy', and stripes streaks and flecks of white, near 159D, or lighter yellows, near 11C and near 11D. The basal area is Chrome Yellow, near 15D, and the point of attachment is Buttercup Yellow, near 15B. The reverse has some stripes, streaks and flecks of Empire Yellow, near 11D, and some of white, near 159D, as well as areas showing through that appear Chinese Coral, near 32D and a few that appear Carrot Red, near 29C. The basal area is a darker Chrome Yellow, near 14D, and the point of attachment is a very deep yellow, near 11A.

The orange-red coloring of the intermediate petals is a little lighter, near 32A, Indian Orange. The yellows are near the same as the outer petals. The stripes, streaks and flecks of inner petals appears more red, near 43A, Signal Red, and a color between 43A and 33A, and the yellows are often more orange, being near 15D, a Chrome Yellow. The basal area is near 15D and the point of attachment is near 15B, Buttercup Yellow. The reverse has some stripes, streaks and flecks of near 11C and near 11D, and near 41D, a light Mandarin Red. Basal area is near 12C, Aureolin, and darker at the point of attachment, near 12A.

As the bloom ages the most noticeable colors go to near 40A, Dutch Vermilion, and a pure white at the center of the flower and near 52A, Crimson, and near 52B, Carmen, and pure white on the outer petals. Just before the petals drop, stripes streaks and flecks are pure white and Carmine Rose, near 52C and near 52D. The basal area is Sulphur Yellow, near 6C, and white, near 155D. The point of attachment is near 4D, Primrose Yellow. The reverse is near pure white and Venetian Pink, near 49C, and French Rose, near 49D, with a basal area of near 155D and 11D, and point of attachment, near 11C.

There is little or no further fade before the petals drop.

Varying soil conditions, light intensity and other varying climatic conditions does alter the yellow tonation in the colors of the flowers, as well as the petal count and the degree of bronze on the new foliage.

The general tonality of this rose is orange-red and white stripes with some yellow, especially near the center of the flowers. From a distance, this rose may appear red and white striped or, under optimum conditions, orange and white striped.

Petaloids: The texture is the same as that of the petals.

There are 1 to 9 petaloids with 4 being the most common number found.

*Size.*—Width is 3/32- to 1/2-inch at the widest point and 9/32- to 15/16-inch long

*Unique characteristics.*—Petaloides are deformed petals, following no pattern. They may be half a petal either vertically or horizontally. They may have a lobed outer margin. They may be epipetalous, having what appears to be an anther where the main vein should be. Occasionally they are attached to the receptacle by a filament.

Peduncle: The aspect is straight and its strength is strong. The length varies from 1 1/4- to 1 1/2-inches. The diameter is 3/32- to 4/32-inch, becoming 4/32- to 5/32-inch just below the receptacle. The appearance is semi-glossy with numerous stipitate glands and some fine hairs. The color is Lettuce Green, near 144A, and may be flushed with a greyed-purple anthocyanin coloration, between 184B and 185B, but only on one side.

Receptacle: The receptacle is funnel shaped. Its width varies from 7/32- to 9/32-inch but is most often 9/32-inch. Length is 5/16- to 6/16-inch. The appearance is semi-glossy with tiny, fine, appressed hairs in straight rows. The color is Lettuce Green, near 144A, and often has some anthocyanin coloring present, between 184B and 185B.

The top surface of the receptacle is circular with a diameter of around 5/16-inch. The color of the surface is near 2D, a very light green-yellow.

REPRODUCTIVE ORGANS

Stamens, filaments and anthers: Regularly attached along the outer edge of the receptacle, adjacent to the petals, they are numerous in quantity, 135 to 160.

Filaments are very thin and 2/16- to 5/16-inch long. Their color is the same as the receptacle to which they are attached, near 2D.

Anthers are near 21B, Maize Yellow and pollen is near 17B, Indian Yellow. The quantity of pollen is only some.

Pistils, styles and stigmas: There are only 26 to 30 in quantity.

Styles are thin and straight and bunched together in an alveola in the center of the receptacle's surface. The majority are around 3/32-inch long. There are a few that are around 4/32-inch long and a few around the outer edge of the bunch that are 5/32-inch long. The color of both the styles and the stigmas is also, near 2D.

Hips: The shape is generally somewhat globose with an oblique base. Occasionally the shape may be oblate, but always with a truncate top. Hips have been measured at 13/16-inch in diameter and 27/32-inch deep, 25/32-inch diameter and depth, and 23/32-inch diameter and 5/8-inch deep.

Surface texture is glabrous, matte and may have scabrid areas. As the hips start to mature, they become flushed near 163A and near 163B, from the greyed-orange group. When fully ripe the colors are near Tangerine Orange, near 24A, Marigold Orange, near 28B, and Persimmon Orange, near 28A. Seeds do not protrude from the hip.

PLANT

Habit and growth: 'SPRolife' is an upright and uniformly, well branched plant. Its growth is very vigorous. It can reach and maintain a height of 5 to 6 feet. Some of the individual canes have been measured up to 5 feet 7 inches long. All canes eventually terminate in a cluster of buds and flowers. The weight of the clusters of buds and flowers usually causes the canes to arch, extending about 3 feet from the center of the plant. In this manner, the plant can reach to 6 feet wide. Laterals from near the base of the arched stems, quickly grow upward to give the plant its 5 to 6 foot height. New growth further up the canes is most often shorter, in varying lengths, starting as short as 2-inches.

Root initiation from cuttings in controlled greenhouse conditions takes 6 to 10 days.

Foliage: Pinnately compound with 7 leaflets, occasionally with 3 leaflets and even less frequently with 5 leaflets.

*Quantity.*—Foliage is abundant. The length of the internodes on the main stalks is 11/16- to 1-inch, giving 5 to 7 leaves per five inches of stem length. On the laterals, spacing varies from 7/16- to 11/16 inch.

Size of mature leaf, from stem to tip, measures 4½-inches to 5¼-inches when measured along the rachis. The mature terminal leaflet measures ⅞- to 1 5/16-inches wide at its widest point and 1 11/16- to 2⅝-inches long.

Leaflets are narrow, ovate-lanceolate with an acuminate apex and narrowly ovate base.

*Margin.*—Serration is fine, single and uneven.

*Color of the foliage.*—Anthocyanin coloration is strong on the young foliage: Both upper and lower surfaces may appear entirely near 183A from the greyed-purple group or the tips of those leaflets may appear near 146C, a medium yellow-green with the anthocyanin coloration of near 183A increasing in intensity toward the base of the leaflets. In full sun, on the fourth leaf from the growing tip, near 146C becomes the dominant color, flushed with a deeper greyed-purple, near 187A. On the older foliage, the anthocyanin coloration is gone. The upper surface appears near 147A, a very dark yellow-green. The under surface is lighter, a dark yellow-green, near 146A.

*Appearance.*—The upper surface of the new foliage is glossy and looses that gloss as it ages, with the oldest foliage appearing matte. The center vein and primary lateral are depressed. The undersides of the leaflets have the main veins protruding entirely and the secondary veins protruding only slightly. The texture is coriaceous.

Petiole: The color on young leaf, the upper side is near 145B, a pale yellow-green, between the stipules. The groove and ridges above the stipules are near 183A, from the greyed-purple group, or near 145B flushed with near 183 A. The underside is darker, a medium yellow-green, near 146C, and may be flushed with near 175A, from the greyed-orange group.

The color on old leaf, the upper side is a dark yellow-green, near 146A, along the ridges and a very light yellow-green, near 145C, in the groove, down to the stipules when the ridge disappears and the entire petiole is near 145C. The underside is a medium yellow-green, near 144A.

*Texture and appearance.*—Upper side of the mature leaf is glabrous, the underside has 1 to 3 prickles that measure 1/32-inch or may be up to 5/32-inch long, slanted toward the base of the petiole and hooked at the tip. There also may be a number of smaller prickles or stipitate glands.

Rachis: Length is variable, averaging 1½-inches. The color is the same as that part of the petiole above the stipules with the exception that the color in the groove on the upper side of the older leaf is a dark yellow-green, near 146B.

*Texture and appearance of the rachis.*—The upper side is still glabrous. The underside has 4 to 9 prickles hooked and slanted toward the base of the rachis.

Petiolules: The color on young leaf is near 183A from the greyed purple group. The underside is Lettuce Green, near 144A flushed with near 183A. On the old leaf — ridges may still be flushed near 183A but the groove is a medium yellow-green, near 146D. The underside is near 146D.

The length differs by location on the leaf: to the terminal leaf the petiolule is ⅜- to ⅝-inches long with ⅜-inch being the most common length; to the first and third pair of leaflets it is usually 1/32-inch long and to the second pair of leaflets it is usually 1/16-inch long.

Stipules: On mature leaves, the overall length within each pair of stipules located at the base of each petiole is even or near even. They average about 1-inch long and usually not varying in overall length by more than 1/16-inch. Attached lengths are between ⅝- and ⅞-inch. The tips are angled 45° out from the stem, remaining on the same plane. The length angled out ranges from 5/32- to ⅜-inch on side and ⅜- to ⅜-inch on the opposing side. The widths are also variable within each pair, ranging from 5/32-inch and 3/32-inch to 5/32-inch and 6/32-inch.

Margins have an extremely fine serration.

Color is a very dark yellow-green, near 147A, at the outer edges and Scheele's Green, near 144B, adjacent to the petiole. The reverse is near 147A and near 144A adjacent to the petiole. On young leaves the upper side is flushed with a greyed-orange, near 176B or near 175A.

Resistance: 'SPRolife' has very good resistance to powdery mildew, but is susceptible to downy mildew, blackspot, and rust. Resistance to thrip and rose midge appear to be good but the cultivar is susceptible to aphids and spider mites.

Wood: Diameter main stems is 11/32-inch, primary laterals is ⅜- to ½-inch and flowering stems average ¼-inch diameter.

*New wood.*—Texture/appearance is glabrous and glossy. The color is a medium yellow-green, near 146C.

*Old wood.*—The color is a little darker than that of the new growth, being between 147B and 146C. The surface is matte.

Prickles:

*Quantity on main stalks.*—Average 4 to 6 per inch, varying from 3 to 8 and occasionally in two nearly parallel rows with 10 per inch on the same side of the stem. On primary laterals and flowering stems there are 2 or fewer per inch.

Length is randomly variable. Longer prickles may be 7/32-, 8/32- and 9/32-inch in length and shorter ones may be 2/32-inch and 3/32-inch in length. Most of the prickles are these lengths. The length of the oblong shaped base is 8/32- to 12/32-inch. The prickle quickly tapers from that base length to 3/32- and then to a point, angled down and usually hooked or curved downward at the tip.

Color when young is near 182A, from the greyed-red group and when old, near 199D, from the grey-brown group. Those on the underside of the rachis/petiole, when young, are near 182C.

Hardiness: Tested hardy in zones 5 through 9, with winter protection recommended where temperatures go below freezing for extended periods. Plants held up very well under testing in American Horticultural Society heat zones 9 through 1.

It is claimed:

1. A new and distinct variety of hard, miniature rose plant is claimed, substantially as herein illustrated and described, characterized particularly as to novelty by the unique combination of its miniature-sized, orange-red and white striped flowers borne in large clusters on long and arching canes with abundant, miniature-sized leaves, and having very good resistance to powdery mildew.

* * * * *

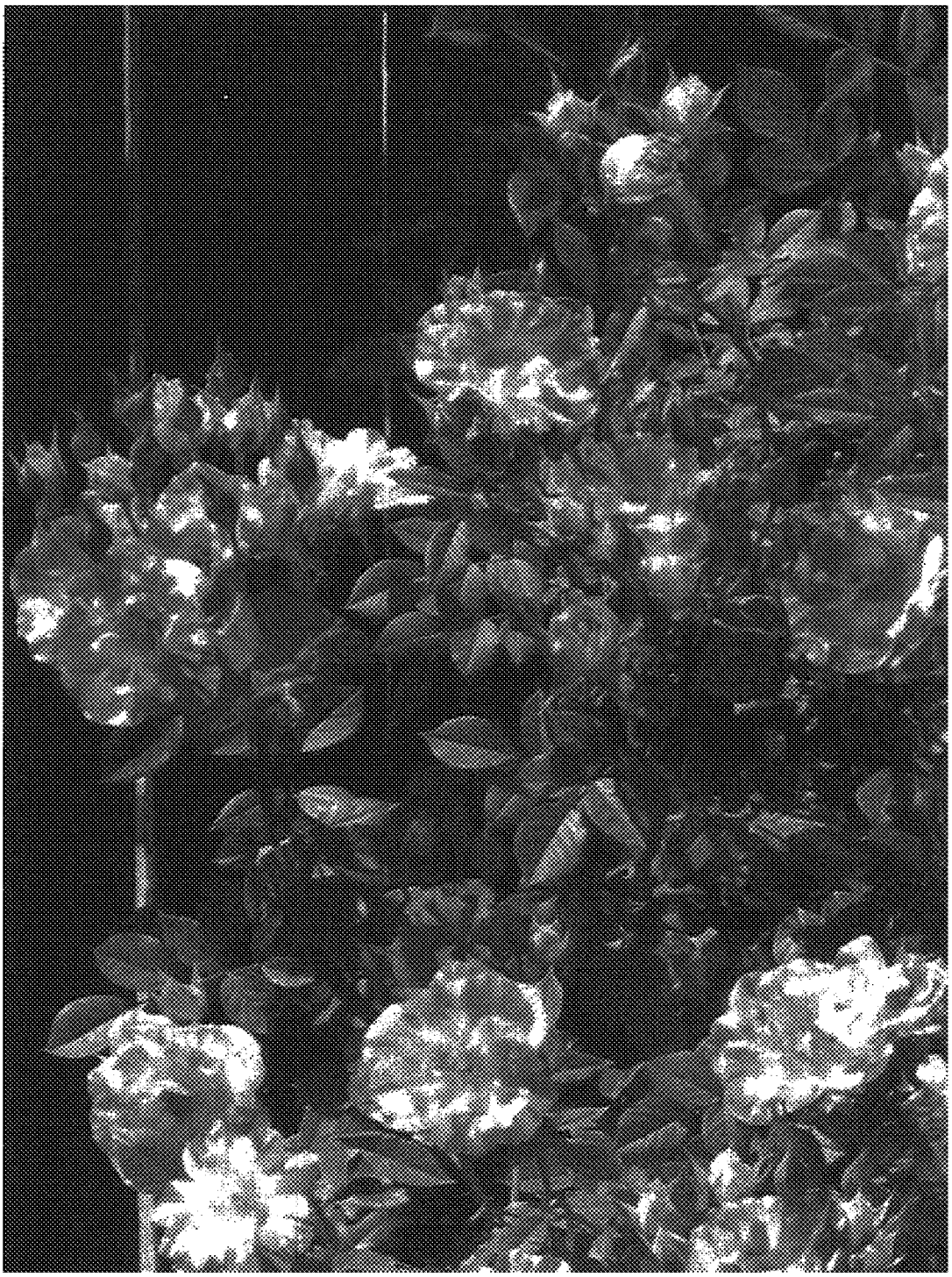

UNITED STATES PATENT AND TRADEMARK OFFICE

CERTIFICATE OF CORRECTION

PATENT NO. : PP 17,908 P3
APPLICATION NO. : 11/201618
DATED : August 7, 2007
INVENTOR(S) : James Sproul It is certified that error appears in the above-identified patent and that said Letters Patent is hereby corrected as shown below:

Column 1, Line 34: the words “red white” should read --red and white--

Signed and Sealed this

Eighteenth Day of December, 2007

JON W. DUDAS
*Director of the United States Patent and Trademark Office*